(12) United States Patent
Zueger

(10) Patent No.: US 10,161,858 B2
(45) Date of Patent: Dec. 25, 2018

(54) PROCESS MONITORING FOR UV CURING

(71) Applicant: Oerlikon Surface Solutions AG, Pfaffikon, Pfäffikon SZ (CH)

(72) Inventor: Othmar Zueger, Triesen (LI)

(73) Assignee: OERLIKON SURFACE SOLUTIONS AG, PFÄFFIKON, Pfäffikon SZ (CH)

( * ) Notice: Subject to any disclaimer, the term of this patent is extended or adjusted under 35 U.S.C. 154(b) by 0 days.

(21) Appl. No.: 15/521,628

(22) PCT Filed: Nov. 24, 2015

(86) PCT No.: PCT/EP2015/077445
§ 371 (c)(1),
(2) Date: Apr. 25, 2017

(87) PCT Pub. No.: WO2016/083342
PCT Pub. Date: Jun. 2, 2016

(65) Prior Publication Data
US 2017/0254745 A1 Sep. 7, 2017

Related U.S. Application Data

(60) Provisional application No. 62/084,004, filed on Nov. 25, 2014.

(51) Int. Cl.
*G01N 21/33* (2006.01)
*G01N 21/84* (2006.01)

(52) U.S. Cl.
CPC ......... *G01N 21/33* (2013.01); *G01N 21/8422* (2013.01); *G01N 2021/845* (2013.01); *G01N 2021/8411* (2013.01); *G01N 2021/8427* (2013.01); *G01N 2201/0636* (2013.01)

(58) Field of Classification Search
CPC ............... G01N 21/33; G01N 21/8422; G01N 2021/8411
See application file for complete search history.

(56) References Cited

U.S. PATENT DOCUMENTS

2005/0143483 A1   6/2005   Sanuki
2006/0044555 A1   3/2006   Wang
(Continued)

FOREIGN PATENT DOCUMENTS

DE   10 2010 061 767 A1   5/2012
EP          0 927 726 B1   7/1999
EP          2 664 910 A2  11/2013

OTHER PUBLICATIONS

International Search Report for PCT/EP2015/077445 dated Feb. 8, 2016.

*Primary Examiner* — Hugh H Maupin
(74) *Attorney, Agent, or Firm* — Pearne & Gordon LLP

(57) ABSTRACT

An in-situ process-monitoring device for measuring a curing state of components coated with a UV-curable lacquer. The device includes at least one radiation source for curing the lacquer, as well as at least one signal source and at least one spectrometer for measuring radiation of the signal source reflected from the components, in order to determine the curing state. The measuring is carried out in a contactless manner, and the at least one signal source for the measuring is identical to the at least one radiation source for the curing.

13 Claims, 7 Drawing Sheets

(56) References Cited

U.S. PATENT DOCUMENTS

| | | | | |
|---|---|---|---|---|
| 2009/0323056 A1* | 12/2009 | Yun | ............................ | G01J 3/26 |
| | | | | 356/301 |
| 2014/0044889 A1* | 2/2014 | Qi | ...................... | C23C 16/45536 |
| | | | | 427/595 |
| 2015/0354132 A1* | 12/2015 | Schweers | .................. | D06N 1/00 |
| | | | | 428/172 |

* cited by examiner

PROCESS MONITORING FOR UV CURING

The invention relates to a new in-situ process-monitoring device for UV-curable lacquers on components.

During curing of UV-sensitive lacquer films on components, a lacquer-specific UV dose must be exceeded as a product of the UV light intensity falling onto the lacquer surface and of the time of the irradiation, so that a complete reaction (polymerization) of the viscous liquid lacquer film occurs to form a solid surface coating. In the case of incomplete curing, required mechanical properties of the lacquer coating, such as hardness and scratch resistance, are not achieved; likewise, the adhesion strength or other properties cannot be achieved, or are achieved only incompletely, because of incomplete polymerization. In industrial applications of such lacquer coatings on components, for cost and production processes it is possible to check these characteristics only on individual samples. In the case of insufficient hardening, it must be assumed that at least a considerable number of components produced since the date of the last test may have qualitative defects and are therefore lost as rejects.

For this reason, it is very desirable in industrial applications to have a test or monitoring device integrated in the production process and a method for measuring the properties of the UV-exposed film as a surface layer so as to ensure without any delays the quality of the components. Even more desirable for this monitoring device and method is the possibility of being able to track the continuous curing process of the lacquer film during the UV exposure by means of measuring signals. With such monitoring, the curing process can be controlled, in the simplest case the curing time can be adjusted in a controlled manner. The latter can thus be kept, in a regulated manner, as short as necessary for complete curing. In this way, it is possible to achieve the highest possible productivity with a constant quality for the curing step. In the case of exposure with a fixed curing time, for reasons of process safety, it is necessary to keep longer than minimum in order to ensure complete curing in every case in the event of variations in the process. In a further version of a monitoring of the curing state, other process parameters can also be influenced through control technology, for example the power of the UV light source or the speed at which the components are moved through the UV exposure area. In this way, a minimum process time for complete curing can be achieved, thus maximizing productivity.

With such a process monitoring, it is usually not possible to directly measure the cured lacquer film's mostly mechanical properties to be achieved, since they should primarily take place in a contactless manner. Only related properties can be measured with such methods, which make it possible to infer with certainty that the necessary properties have been complied with. A common method for determining the degree of curing is optical spectroscopy, in which the change in reflection (or transmission) of the light incident on the lacquer film is analyzed by means of spectral resolution measuring devices. These spectral changes are varnish specific in different wavelength ranges. Examples of the UV range are given in a brochure from the company Microchemicals GmbH, Ulm, Germany (http://www.microchemicals.com/technicaljnformation/exposure_photoresist.pdf), resp. for the infrared range by BL Grunden in the dissertation "Cure characterization of an unsaturated polyester resin using near-infrared, fluorescence and UV/visible reflection spectroscopies", (Dissertation Thesis 9924301, The University of Connecticut, 1999).

Suitable measuring devices are typically lattice spectrometers or Fourier Transform spectrometers as described in "On-line monitoring of the acrylate conversion in UV photopolymerization by near-infrared reflection spectroscopy" by Scherzer, Mehnert and Lucht (Polymer Spectroscopy Volume 205, pp. 151-162, 2004), or light sensors in combination with adapted optical filter elements. During curing of the lacquer film, the spectra change in certain areas. These changes are used as a quantitative measure for the degree of curing.

Such process monitoring cannot completely replace a random quality assurance. However, by comparing the spectroscopic properties with the technically relevant lacquer properties from random samples, it is possible to match and the spectroscopic data can thus be used for a continuous monitoring of the quality of the lacquer film, which can serve in an extended form as mentioned above for controlling the process.

The properties of the surface coatings on components are tested randomly, outside the production process, using direct methods of testing mechanical properties that usually destroy the coating, or also non-destructive methods that measure other properties that, based on experience, are directly related to the necessary properties.

Among the non-destructive methods, optical methods in particular are known, as described in detail in a brochure from the company Microchemicals GmbH, Ulm, Germany (http://www.microchemtcals.com/technicalInformation/exposurephotoresist.pdf). When UV lacquer films are cured, a polymerization reaction occurs in which polymer chains are formed from the monomers/oligomers in the viscous fluid lacquer, with the structural change also causing a change in the optical properties of the lacquer film. In the case of UV-induced curing, some of the UV light wavelengths are absorbed as a function of wavelength. This absorption behavior changes with the degree of curing and can be detected as a change in the wavelength-dependent reflection behavior (reflection spectrum) with the aid of spectrometers. Examples for the UV range are described in a brochure from the company Microchemicals GmbH, Ulm, Germany (http://www.microchemicals.com/technical_information/exposure_photoresist.pdf), resp. for the infrared range by BL Grunden in the dissertation "Cure characterization of an unsaturated polyester resin using near-infrared, fluorescence and UV/visible reflection spectroscopies", (Dissertation/Thesis 9924301, The University of Connecticut, 1999). UV spectrometers with cell detectors are particularly suitable for this purpose, since these reflection spectra of the entire UV wavelength range of 230 . . . 400 nm can be measured within up to less than 10 milliseconds.

Spectrometers with the same structure, but array detectors for the near-infrared range of 800 . . . 1700 nm (NIR), are available nowadays and can be operated with similar read-out data. Thus, changes in the spectral reflection behavior in the NIR region during the curing process can be monitored simultaneously with UV exposure, as described in "On-line monitoring of the acrylate conversion in UV photo-polymerization by near-infrared reflection spectroscopy" by Scherzer, Mehner and Lucht (Polymer Spectroscopy Volume 205, pp. 151-162, 2004).

In the infrared range IR (1500 . . . 20,000 nm), excitation bands change with the conversion of the viscous lacquer into the cured coating, which is shown as a change in the infrared reflectivity spectrum. In a particular wave-width band, a well-measurable change takes place by means of which the curing state of the lacquer film can be determined. See Lowry and Weesner (Using Real-Time FT-IR to Characterize UV Curable Optical Adhesives, Spectroscopy, Vol. 26, Iss. 8, pp. 40-46, 2011). Nowadays, infrared spectra are almost exclusively measured using Fourier Transform infrared spectrometers (FTIR).

For specific applications, spectral changes in reflection can also be detected using one or more suitable optical filters and simple optical intensity sensors, but the filters must be specifically adapted to the application and the spectral properties of the light deflection of the lacquer film. For industrial applications, this simple but only specifically applicable solution can make sense as a more economical and robust solution instead of a broadband spectrometer. The following disadvantages result in particular from the prior art:

Without monitoring equipment, only a delayed recognition of quality problems can only be achieved by random sample measurements on produced parts.

Furthermore, a prolonged exposure time is required to reliably reach the required exposure dose.

In addition, there is the risk of over-exposure of the lacquer film, which can lead to embrittlement.

To date, there is no or only delayed early detection of process drifts, which can lead to serious quality problems.

According to the invention, a radiation source which is used for curing the lacquer is simultaneously used as a signal source for the measurement of the degree of curing. Among others, this has the advantage that the orientation of the light-reflecting surface plays a subordinate role and that the light always arrives at the detector. This is particularly advantageous when the substrates are mounted on rotating spindles.

According to a particularly preferred embodiment, the hardening layer is directed onto the substrates via a segmented mirror, the latter appearing to be continuous along the original direction but appearing with an aperture in the projection along the radiation reflected by the substrate. Aperture means, for example, a hole or a plurality of holes, a gap or several gaps, or a combination of one or more gaps and/or one or more holes. Slits are also possible.

BRIEF DESCRIPTION OF THE DRAWINGS

Hereinafter, the invention is complemented in detail and by way of example on the basis of figures.

DETAILED DESCRIPTION

Figure 1:
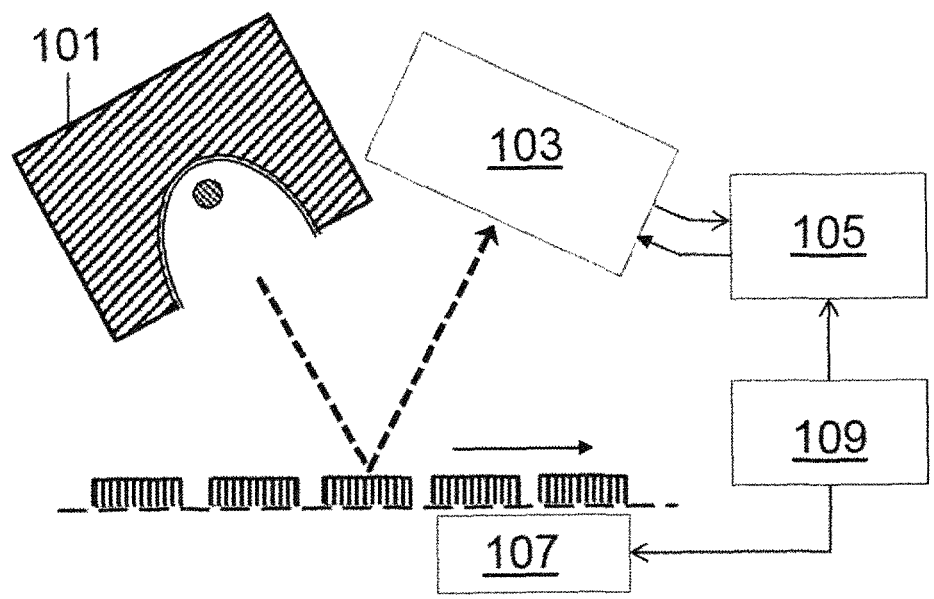
FIG. 1: Schematic representation of the automated detection of a curing state of a UV-curable lacquer film on components.

Such an inventive automated detection of the degree of curing of a UV-curable lacquer film on components is shown schematically in FIG. 1. The components are sequentially moved into the light beam of a UV light source 101. There, the components linger for a certain time interval, during which the lacquer film is exposed to UV light for the curing. Part of the radiation emitted by the UV source is reflected at the surface of the lacquer film and can be detected with a suitably arranged wavelength-selective light sensor array (spectrometer) 103. Highly intensive UV sources are based on gas discharge lamps whose plasma not only emits UV light but also at least equally strong visible light and infrared radiation. For this reason, the UV light source serves at the same time as a source for the reflection light to be analyzed, and the light source used in spectrometers usually does not have to be used for the measuring beam.

During the exposure time interval, a plurality of spectra (at least 2) are measured and fed to a monitoring unit 105 which automatically compares the spectra and calculates the degree of curing from these spectral data by means of a suitable algorithm from the spectral changes. Upon reaching a certain, predetermined degree of hardening, a signal is sent to drive the feed of the components 107, which performs the changeover to the next component.

With this hardening carried out with standing components, this is usually not very homogeneous, since the illumination of the component surface becomes uneven with conventional UV sources which extend in the direction perpendicular to the direction of movement of the components, in particular with components having a length which is significantly greater than the extent of the illuminating range or length of the UV sources.

Figure 2:
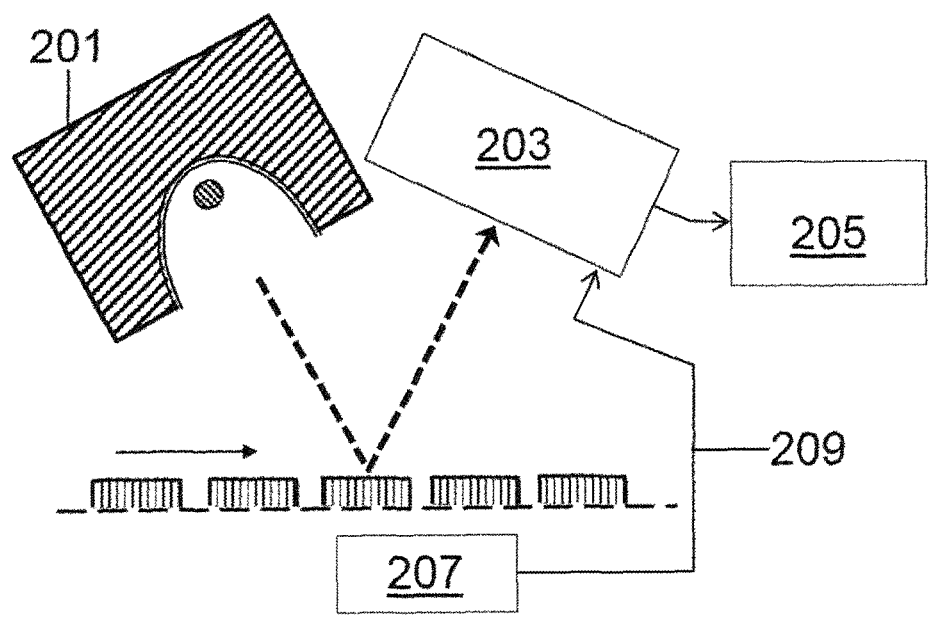
FIG. 2: Schematic representation of a synchronization for moving components for the automated detection of a curing state of a UV-curable lacquer film, in which a sensor detects the position of the component and a trigger signal 209 generates the individual spectral images for a series of predefined, successive positions.

It is advantageous to move the components continuously through the illumination region, since a substantially better homogeneity can thus be obtained. If reflection spectra are recorded simultaneously with the monitoring unit 203 during this continuous movement, this recording cycle should be synchronized with the movement of the components. This allows the reflection behavior to be measured in the same way for all successively exposed components. FIG. 2 shows schematically such a synchronization with the movement, by measuring the position of the component with a sensor and generating a trigger signal 209 for the individual spectral recordings for a series of predefined, successive positions.

Since the reflected intensity can change continuously with the movement of the components due to the surface geometry, the recording rate must be faster than the rate at which the components are moved past the UV source through the illumination area. This change in the detected intensity leads to a modulation of the intensity both during the recording of a spectrum as well as from successive spectra. For the comparison of the spectra for the detection of the degree of curing, it is advantageous not to compare the spectral data directly as an intensity spectrum, but in a mathematically converted form in which the direct dependence on the absolute intensity is suppressed. Possible forms lie in the logarithmic intensity Ln [1($\lambda$)] or in the logarithmic derivative of the intensity spectra I($\lambda$) according to the wavelengths $\lambda$, $\delta$ Ln [1($\lambda$)]/$\delta\lambda$, where Ln denotes the natural logarithmic function. While the spectrum Ln [1($\lambda$)] shifts by an amount with changing absolute intensity, the spectrum Ln [I($\lambda$)]/$\delta\lambda$ has the property that regardless of the current intensity, at each wavelength the signal remains essentially the same, because the differential in relation to the derivation $\delta$ Ln [1($\lambda$)]/$\delta\lambda$ also offsets a shift of the spectrum Ln [1($\lambda$)]. Other methods can also be used for the comparison of spectra, for example, numerical fit algorithms, in which the measured spectrum compares with a predetermined spectra calculated according to a suitable model. These fit algorithms can contain a wavelength-dependent scaling factor as a numerical optimization parameter, which is treated as an additional degree of freedom in the comparison algorithm of the spectra.

In the case of UV-VIS-NIR lattice spectrometers with detector array sensor, a rate of some 10 up to 100 spectra per second can be achieved, i.e. a plurality of spectra are measured in each case during an exposure of typically 1 . . . 100 seconds, depending on the lacquer, UV source, geometrical arrangement, and so the gradual curing from temporal changes of reflection signals in particular wavelength regions is detected.

In the case of a Fourier transform spectrometer, as used in the infrared range, spectral rates of 1 . . . 100 per second can be achieved with fast-scanning instruments. Since the typical spectral regions in which the changes are visible are not very narrow (typically some 100 cm$^{-1}$), it is possible to work in a low-resolution mode with a lower interferometer phase scan range (in the simplest case, a linear motion of a mirror of the interferometer), whereby the scanning speed can be increased since this is limited by the mechanics of the movement of a part of the interferometer by the inertia of this movable element (in the simplest case a linear movement of a mirror).

In the case of the detection of spectral changes by means of discrete optical filters together with simple intensity sensors, a plurality of wavelength ranges must be simultaneously measured in order to detect spectral changes in the reflection due to increasing curing. Intensity sensors usually have a significantly higher range of signal dynamics than array sensors. These therefore have hardly practical limits on repetition rates of signal acquisition in this application, in which the minimum exposure time for complete curing is the relevant time limitation which, as mentioned above, is in real applications in the range of 1 to 1 . . . 100 sec.

In order to achieve high productivity in the exposure of components, mainly high-intensity UV sources with intensity distribution over the entire UV range with wavelengths $\lambda$, of 200 . . . 400 nm are used. Such sources usually consist of high-performance metal halide lamps in which a plasma which emits the UV light is electrically excited, in combination with optical reflecting elements that bundle the UV light into the application area in front of the lamp. The components to be exposed, whose surface is provided with UV lacquer, are brought into this area of application for the exposure. These UV sources can either be designed as linear sources with a particular tubular lamp and a correspondingly shaped elongated mirror element, or they can also consist of a series of juxtaposed UV sources, each with a point-shaped lamp and a suitable reflector to it. In addition to the desired UV light (<20%), these metal halide lamps also emit intense visible (-10%) and infrared (>70%) radiation. This intense infrared radiation leads to a heating of the components. In the case of plastic parts whose plastic material allows a maximum temperature of <100° C., the exposure has to take place in such a way that the necessary UV dose is applied over time in such a way that the components remain below the critical phase-conversion temperature.

Figure 3:
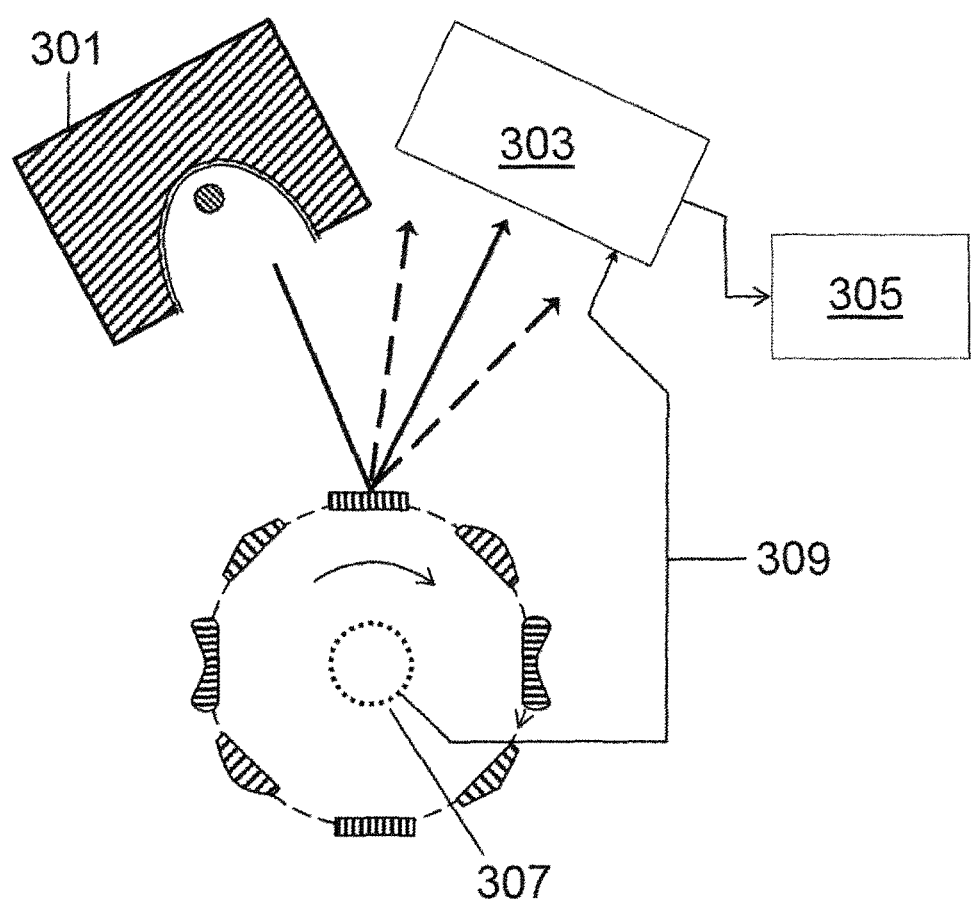
FIG. 3: Schematic representation of the automated detection of a curing state of a UV-curable lacquer film on components with an arrangement on a rotating spindle-shaped holder.

The problem of the high heating during the exposure can be circumvented as follows. On the one hand, the components are not continuously exposed to the UV radiation by being cycled into the region of high intensity so that they can cool down periodically in the period of time in which they are outside the exposure range. This cyclic movement of the components is predominantly achieved by arranging the components on a spindle-shaped holder and rotating this holder around its own axis (FIG. 3).

Figure 4:
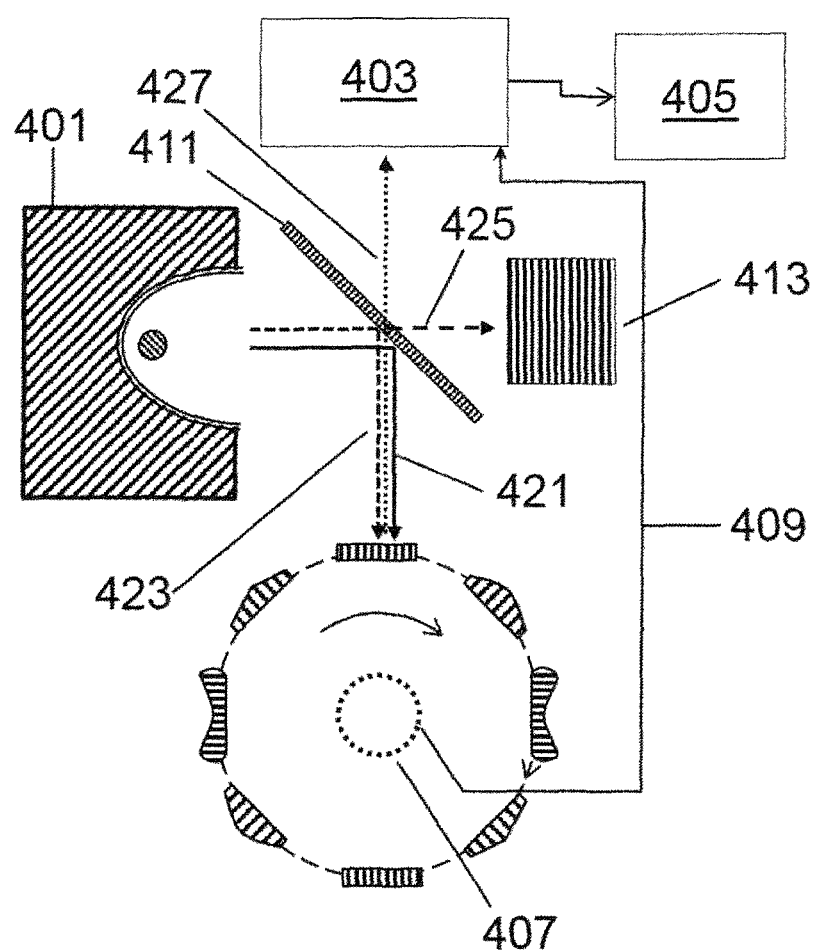
FIG. 4: Schematic representation of an in-situ process monitoring device for detecting the curing state of a UV-curable lacquer film on components using a dichroic mirror 411.

Of course, the arrangement of the components on a spindle is not the only way to move the parts cyclically through the application area: with an arrangement of the components on a rotating disk or active linear cyclic forward and backward motions of the components on a linear transport system, it is possible to achieve essentially the same. On the other hand, the UV light can be selectively reflected by a suitably coated dichroic mirror element 411, which is arranged between the UV source and the application area, and the visible and infrared light 425 are kept away from the application area by selective transmission in the mirror element (FIG. 4).

With such a dichroic mirror element, the visible and infrared radiation can typically be suppressed to over 80%, while simultaneously the UV radiation 421 is directed efficiently into the area of application. Even with this attenuation, a considerable amount of IR light 423 still enters the application area. The relative proportion of the total light in the application area is, however, typically still 30 to 50%.

For monitoring the reflection spectra in the relevant infrared range, this light serves as a source for determining the degree of reflection of the lacquer layer.

In contrast to the conventional application of IR spectrometers in which an internal IR source is installed, this is not used in the monitoring application shown here, but it is rather directly the IR light 427 emitted by the UV lamp that is used.

With the arrangement of the components on a rotating spindle, because of the simultaneous movement of the whole spindle, a stepwise movement as described above is technically more demanding for the spectral detection of the reflected light with a monitoring system due to the mechanical inertia. Substantially simpler is a continuous rotary movement. As long as the peripheral speed of the components on the spindle is sufficiently slow so that the components move only slightly (as compared to their own size) during a measuring cycle of the spectrometer, it can be assumed that the detected spectrum is only slightly different from a statically measured spectrum. Typical recording times for a spectrum are both with detector arrays in lattice spectrometers or also fast-scanning FTIR spectrometers in the range from a few milliseconds to a few tens of milliseconds, peripheral speeds on spindles typically range from 100 to 500 mm/s. i.e. during a recording scan of the spectrometer, the movement is typically 1 ... 10 mm, which is small compared to its own size for typical component sizes. If, for the further numerical evaluation of the data as described above, it is not the reflected intensity $I(\lambda)$ that is used but a derived value such as e.g. $\delta \, Ln(1)/\delta\lambda$, which is independent of the absolute intensity, it is possible to suppress the intensity fluctuations occurring during the recording of the spectrum through the simultaneous movement of the components with the variables $Ln(1)$ or $\delta \, Ln(1)/\delta\lambda$. It is, of course, advantageous for a high spectral signal stability to have as high a recording scan rate as possible, whereby the intensity fluctuations become relatively smaller, and are to be averaged accordingly over several spectra rather than the choice of a slower rate with higher intensity fluctuations since the signal distortions are minimized, In the case of an FTIR spectrometer, a reflection intensity that fluctuates during the scan results in a modulation of the interferogram, which manifests itself in the Fourier transform as a convolution with a short-wave widening of the resolution function. Since the modulation rate is of the order of the scan rate, this convolution leads to a minimal peak broadening in the reflection spectrum. Since, however, the spectral characteristics of the lacquer are not very narrowband, and thus also do not change as a result of the curing reaction of the lacquer, the adulterations caused by the reflective intensities slightly changing during the scan are small and therefore of secondary importance for monitoring the degree of curing of the lacquer.

However, the preferably used version of FIG. 4 with a dichroic UV mirror 411 in combination with a rotating spindle has the restriction that the light reflected by the lacquer film on the component, which is to be detected by the spectrometer, must be transmitted through the dichroic UV mirror. The dichroic coating of the mirror does not allow the UV light to pass through, but it is transparent for visible and near infrared light (NIR) up to wavelengths of approx. 2500 ... 3000 nm 427. Long-wave infrared light is absorbed by the glass substrates of the UV mirror used and can no longer reach a spectrometer behind it. Although there are UV mirror substrate materials with high infrared transparency, these are very costly, especially in sizes of several 10 cm in extent (e.g. zinc sulfide).

By means of conventional glasses for the UV mirror, monitoring of the curing state of the lacquer film can therefore be achieved only to a limited extent on the NIR wavelength band, but the typical spectral changes in the longer-wavelength IR on the other hand not.

Figure 5:
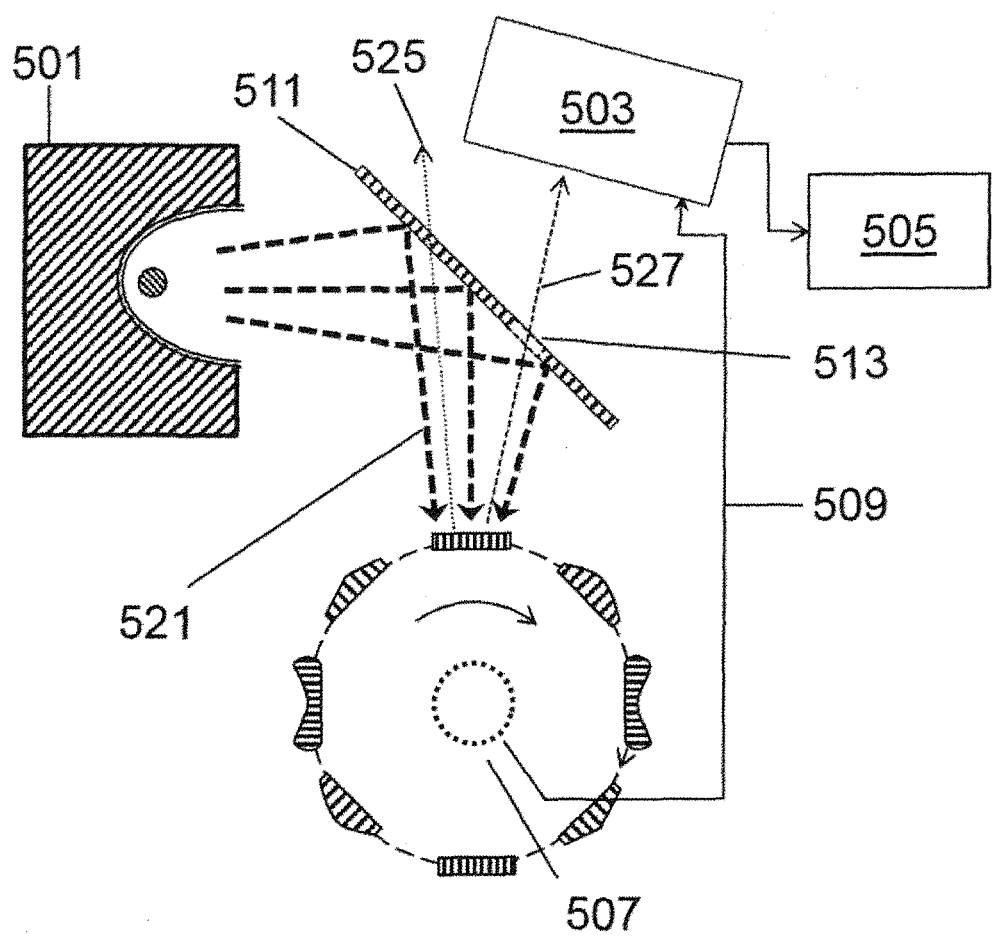
FIG. 5: Schematic representation of an in-situ process monitoring device for detecting the curing state of a UV-curable lacquer film on components, wherein the curing takes place by means of UV exposure by reflection on a dichroic mirror 511 and a hole in the mirror 513 lets through a fraction of the IR radiation 527 reflected by the component surface to the spectrometer 503.

Therefore, it is desirable to have a configuration in which high reflection for the UV light of the source can still be achieved, but the reflected light can be detected without transmission through an optical element with a spectrometer, thus yielding the full air penetrating infrared wavelength range of the spectral reflection in the measuring beam. FIG. 5 shows such an embodiment.

With the aid of a hole 513 in the UV mirror, IR light 527 can pass unhindered onto the measurement window of the spectrometer 503 behind the UV mirror. On the one hand, the size of the hole is to be selected in such a way that the light beam reflected by the lacquer film on the component surface encounters the measurement window of the spectrometer during at least the time interval of a spectrometer scan. For this purpose, several holes, gaps or slits can be used in the mirror. On the other hand, the hole should be as small as possible, since the UV mirror is ineffective in this area of the surface and thus locally less UV light from the source 521 falls onto the lacquer film of the components.

Figure 6:
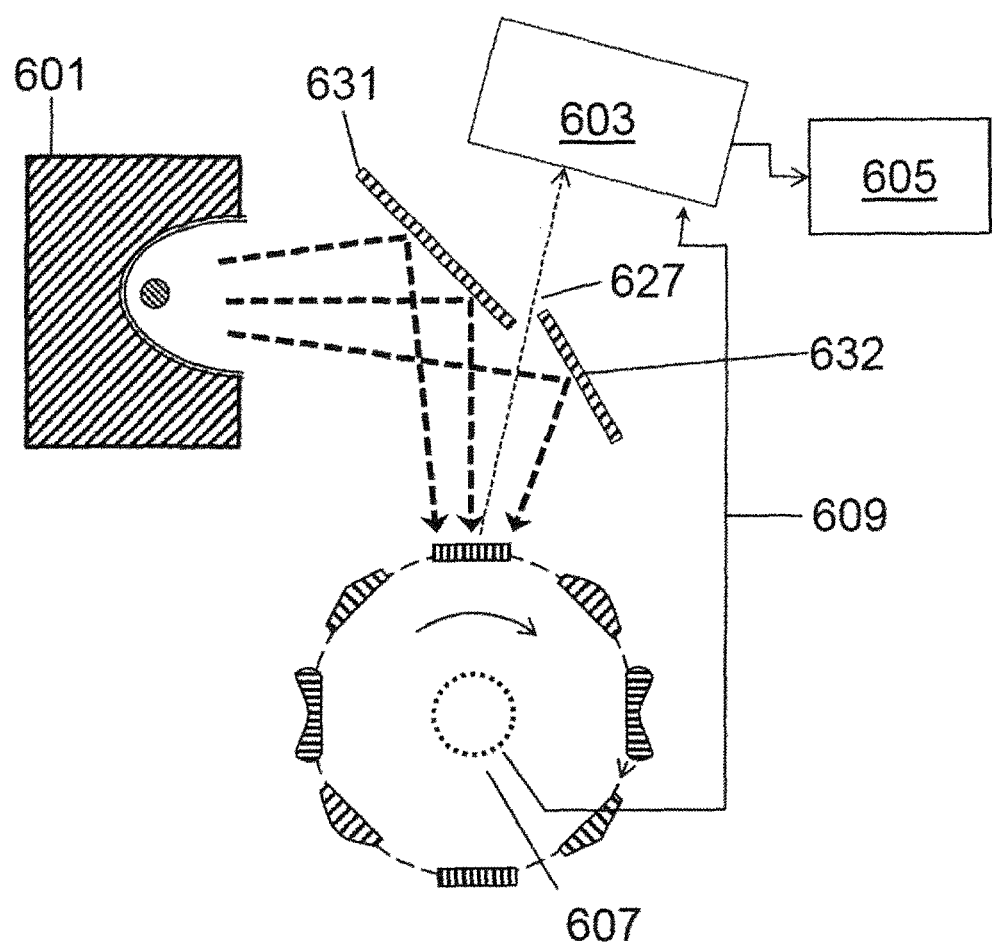
FIG. 6: Schematic representation of an in-situ process monitoring device for detecting the curing state of a UV-curable lacquer film on components, wherein segmented mirror elements 631, 632 optimize the UV exposure by reflection and ensure an increase in the signal quality of the spectrum by increasing the proportion of the measurement signal 627, which falls on the input window of the spectrometer 603 for "in-situ" measurement.

By means of a UV mirror, which instead of a hole consists of at least two segments, arranged at a certain distance (gap) it is possible to eliminate the unevenness of the exposure associated with the hole (FIG. 6). The loss of UV light through the gap aperture can not only be largely eliminated by suitable, different inclination, size and number of mirror segments 631, 632, an optimized arrangement will also allow the UV intensity on the components to be increased, even exceeding the value with a flat, continuous UV mirror. The aperture for the passing through of the retro-reflected light beam can be held so far as to detect as much reflected infrared light 627 as possible without a substantial loss of UV light on the lacquer films to be cured on the component surfaces. This allows more IR light to be applied to the input window of the spectrometer 603, which improves the signal quality of the spectrum for monitoring the curing process. This segmentation of the UV mirror should preferably not be made at the center of the UV mirror, since, on the one hand, the highest UV intensity falls in this region, so that the loss of UV light caused by the gap would be the greatest; on the other hand, in contrast to a central segmentation, the aperture angle for the light reflected by the components can be increased with a non-center segmentation, as shown in FIG. 6 in the upper region and in FIG. 7 in the lower part of the mirror. In this way, the measurement signal can be increased, while simultaneously minimizing the loss of UV light.

Figure 7:
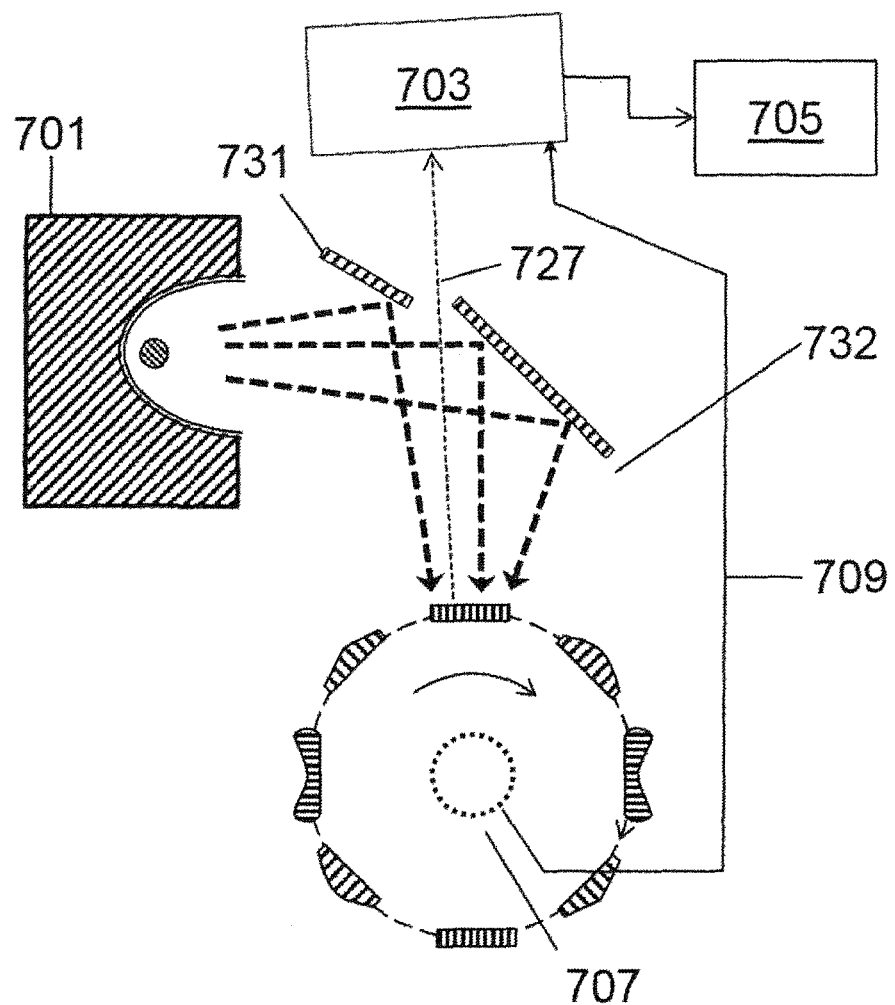
FIG. 7: Schematic representation of an in-situ process monitoring device for detecting the curing state of a UV-curable lacquer coating on components, in a further exemplary mirror arrangement in comparison to FIG. 6.

An arrangement of the spectrometer offset laterally with respect to a continuous mirror element, however, would have a significantly lower intensity yield for the measurement in comparison to the arrangement as described in FIGS. 6 and 7.

Figure 8:
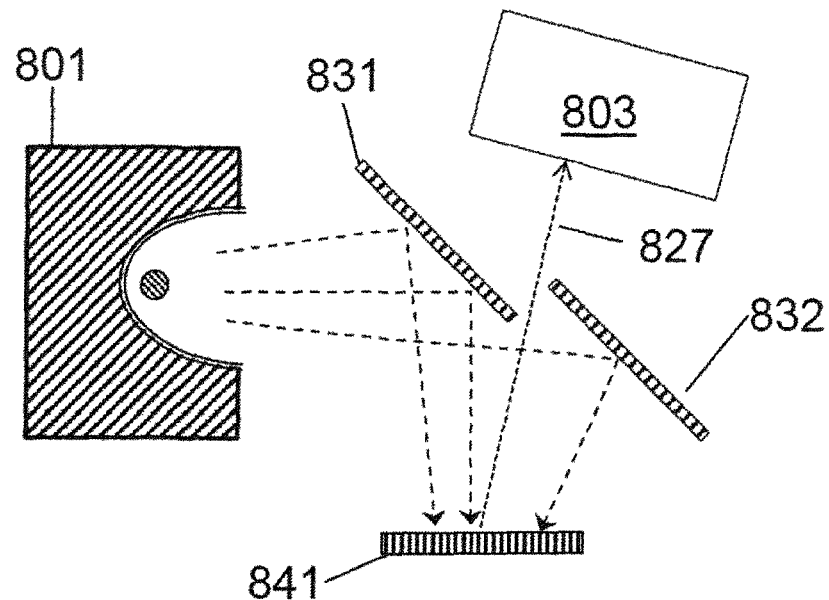
FIG. 8: Schematic representation of the mirror arrangement according to the invention, wherein the segmented mirrors appear in a projection along the original direction of the radiation source, but appear with an aperture in the projection along the radiation reflected by the substrate.

According to a particularly preferred embodiment, the hardening light is directed onto the substrates 841 via a segmented mirror 831 and 832, the latter appearing continuous in the projection along the original direction of the radiation source, but appearing with an aperture in the projection along the radiation reflected by the substrate, and thus part of the radiation reflected from the substrate passes unhindered to the detector 803, as can be seen in FIG. 8.

Figure 9:
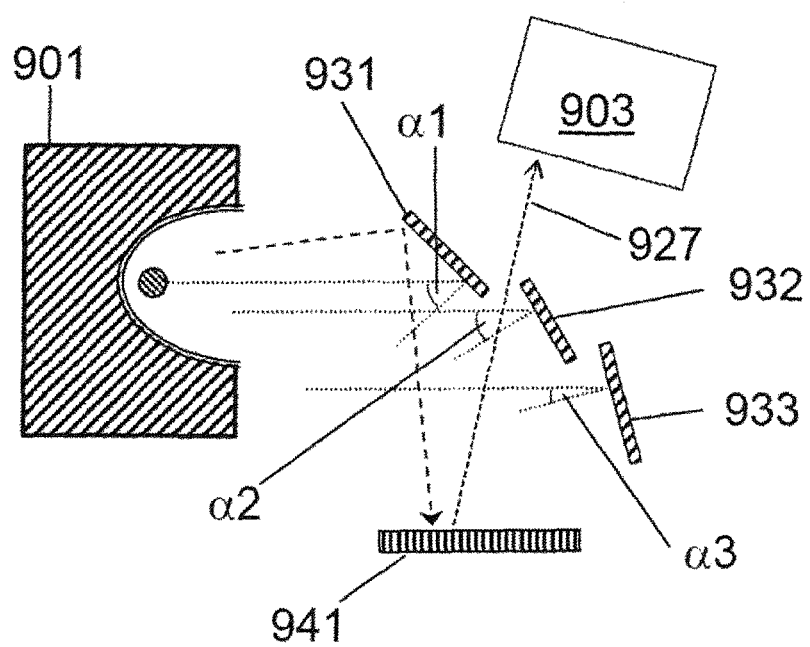
FIG. 9: Schematic representation of an in-situ process monitoring device which shows several segmented mirrors with different tilting.

A particularly preferred embodiment is shown in FIG. 9, wherein at least one or more mirrors 931, 932, 933 can be tilted at angles $\alpha 1, \alpha 2, \ldots \alpha n$, defined between the main optical axis of the radiation source and the normal of the reflecting surface of the mirror, wherein the angle range $0 < \alpha 1, \alpha 2 \ldots \alpha n$ should be $<90°$ and the angles $\alpha 1 \ldots \alpha n$ do not need to be equal.

By monitoring the reflected light of the UV source, the curing state of a lacquer film can be recorded on components in-situ, i.e. during the process, without contact, and thus an online control of the desired lacquer properties to be achieved takes place during the process workflow. This has several advantages in the application in a production process for UV-curable lacquer films on components.

With such a monitoring, the productivity can be increased since it is no longer necessary to expose for a fixed time, but only for the minimum time effectively required for the actual components in order for the lacquer film to be completely cured. In this way, it is possible to avoid exposures that are potentially too short and therefore quality problems in the event that a too short exposure time would be selected on the basis of deviating data. Furthermore, the uniformity of the exposure can also be increased by controlling the exposure process with the aid of monitoring to a specific, predetermined spectral change in the reflection spectrum to be achieved. The highest possible homogeneity is the goal of every mass production process in order to ensure consistently constant properties and qualities of the components.

A further improvement of the inventive process monitoring device lies in the fact that a measuring signal always reaches the spectrometer, i.e. independently of the angle.

The in-situ process motoring device according to the invention can therefore comprise at least one radiation source, at least one signal source, and at least one spectrometer for measuring the curing state of components which are coated with a curable lacquer, characterized in that the measurement can take place in a contact-less manner via spectrometers and the at least one signal source for the measurement is identical to the at least one radiation source, which is used for the curing of the lacquer.

The in-situ process monitoring device can comprise at least one, preferably several, dichroic mirrors.

In the in-situ process monitoring device according to the invention, at least one mirror can be tilted at angles $\alpha 1$, $\alpha 2$, . . . $\alpha n$, defined between the main optical axis of the radiation source and the normal of the reflecting surface of the mirror, characterized in that the angle range $0<\alpha 1$, $\alpha 2$ . . . $\alpha n$ should be $<90°$ and the angles $\alpha 1$ . . . $\alpha n$ do not need to be equal.

The in-situ process monitoring device may have one or more apertures in the mirrors used, which can comprise one or more holes, one or more gaps, one or more slits, or a combination of one or more gaps and/or one or more slits and/or one or more holes.

The in-situ process monitoring device may comprise segmented mirrors which are separated by distances from one another which allow the resulting mirror surface to appear continuous along the original direction of the radiation source, but in the projection along the radiation reflected by the substrate is at least partially unobstructed for the reflected radiation to the spectrometer.

The in-situ process monitoring device according to the invention can comprise one or more lamps as a radiation source which emit radiation in the wavelength range required both for the curing process as well as for measuring the curing process.

The in-situ process monitoring device may comprise a metal halide lamp as the radiation source.

The in-situ process monitoring device may comprise a halogen lamp as the radiation source.

The in-situ process monitoring device can be used for components coated with curable lacquer, which are moved linearly past the curing zone.

The in-situ process monitoring device can be used for components which are coated with curable lacquer, which are moved in rotation past the curing zone.

The in-situ process monitoring device may comprise a trigger unit for triggering the measuring process and a position sensor for measuring the position of the components.

An in-situ process monitoring method for a lacquer curing process on components can use a process monitoring device according to the invention in accordance with one or more of the above-mentioned embodiments.

An in-situ process monitoring method as described above can use a UV-curable lacquer as a curable lacquer on the coated components.

UV source (signal source, radiation source) 101, 201, 301, 401, 501, 601, 701, 801, 901

Spectrally resolving optical sensor unit 103, 203, 303, 403, 503, 603, 703, 803, 903
Reflection Monitoring System 105, 205, 305, 405, 505, 605, 705
Parts Motion Drive 107, 207
Angle Position Sensor 307, 407, 507, 607, 707
Trigger for Spectral Scan 209, 309
Trigger for Gating Mode 409
Trigger Signal 509, 609, 709
Dichroic mirror(s) 411, 511, 631, 632, 731, 732, 831, 832, 931, 932, 933
IR dump 413
UV light 421
Reflected Visible+IR light 423
Transmitted light (Visible+NIR light; 400 . . . 3000 nm) 425, 525
Measurement Signal (Vis+NIR light; 400 . . . 3000 nm) 427
Measurement Signal (UV+Vis+IR light; 250 . . . 50000 nm) 527, 627, 727
Coated components with curable coating 841, 941

What is claimed is:

1. In-situ process monitoring device comprising at least one radiation source, at least one signal source, and at least one spectrometer for measuring the curing state of components which are coated with a curable lacquer, characterized in that the measurement can take place without contact via spectrometers and at least one signal source for the measurement is identical to the at least one radiation source which is used for the curing of the lacquer, wherein a curing time of curable lacquer is adjusted during the cure.

2. In situ process monitoring device according to claim 1, which comprises at least one dichroic mirror.

3. In-situ process monitoring device according to claim 2, wherein the at least one mirror used can be tilted at angles $\alpha 1, \alpha 2, \ldots \alpha n$, defined between the main optical axis of the radiation source and the normal of the reflecting surface of the mirror, characterized in that the angle range $0<\alpha 1$, $\alpha 2 \ldots \alpha n$ should be $<90°$ and the angles $\alpha 1 \ldots \alpha n$ do not need to be equal.

4. In-situ process monitoring device according to claim 1, which comprises at least one dichroic mirror that includes one or more apertures which can comprise one or more holes, one or more gaps, one or more slits or a combination of one or more gaps and/or one or more slits and/or one or more holes.

5. In-situ process monitoring device according to claim 2, wherein the segmented mirrors are separated by distances from one another, characterized in that the resulting mirror surface appears continuous along the original direction of the radiation source, but in the projection along the radiation reflected by the substrate is at least partially unobstructed for the reflected radiation to the spectrometer.

6. In-situ process monitoring device according to claim 1, which comprises one or more lamps as a radiation source which emit radiation in the wavelength range required both for the curing process as well as for measuring the curing process.

7. In-situ process monitoring device according to claim 1, which comprises a metal halide lamp as the radiation source.

8. In-situ process monitoring device according to claim 1, which comprises a halogen lamp as the radiation source.

9. In-situ process monitoring device according to claim 1, wherein the components coated with curable lacquer are moveable in a linear direction past the curing zone.

10. In-situ process monitoring device according to claim 1, in which the components coated with curable lacquer are moveable in rotation past the curing zone.

11. In-situ process monitoring device according to claim 1, which comprises a trigger unit for triggering the measuring process and a position sensor for for measuring the position of the components.

12. In-situ process monitoring method for a lacquer curing process on components that uses a process monitoring device according to claim 1.

13. In-situ process monitoring method according to claim 12, which uses a UV-curable lacquer as a curable lacquer on the coated components.

* * * * *